(12) United States Patent
Park

(10) Patent No.: US 6,643,551 B1
(45) Date of Patent: Nov. 4, 2003

(54) AUTOMATIC THERMAL THERAPEUTIC APPARATUS

(76) Inventor: Sang-kyoo Park, 807-1312, Jugong Apt., Kayang-dong, Kangseo-gu, Seoul 157-200 (KR)

( * ) Notice: Subject to any disclaimer, the term of this patent is extended or adjusted under 35 U.S.C. 154(b) by 0 days.

(21) Appl. No.: 09/958,592

(22) PCT Filed: Jan. 26, 2000

(86) PCT No.: PCT/KR00/00058

§ 371 (c)(1),
(2), (4) Date: Oct. 10, 2001

(87) PCT Pub. No.: WO01/26580

PCT Pub. Date: Apr. 19, 2001

(30) Foreign Application Priority Data

Oct. 14, 1999 (KR) ........................................ 1999/44433

(51) Int. Cl.[7] .............................................. A61H 15/02
(52) U.S. Cl. .......................... 607/100; 601/98; 607/96
(58) Field of Search ........... 607/96, 100; 606/237–245; 601/15, 19, 89, 94

(56) References Cited

U.S. PATENT DOCUMENTS

| | | | | |
|---|---|---|---|---|
| 3,960,145 A | | 6/1976 | Scarbrough ................ | 128/68.1 |
| 5,083,552 A | * | 1/1992 | Lipowitz ..................... | 601/84 |
| 5,330,416 A | * | 7/1994 | Masuda et al. ............... | 601/52 |
| 6,132,392 A | * | 10/2000 | Stone ......................... | 607/115 |
| 6,312,400 B1 | * | 11/2001 | Itikawa et al. .............. | 601/100 |
| 6,387,062 B1 | * | 5/2002 | Moore, Jr. .................. | 601/98 |

FOREIGN PATENT DOCUMENTS

DE          3111345          6/1982

* cited by examiner

*Primary Examiner*—Linda C. M. Dvorak
*Assistant Examiner*—H M. Johnson
(74) *Attorney, Agent, or Firm*—Madson & Metcalf

(57) ABSTRACT

An automatic thermal therapeutic apparatus is disclosed. The thermal therapeutic apparatus includes an upper housing having a recess and a lower housing. A plurality of thermal therapeutic devices are positioned in the recess of the housing. Each thermal therapeutic device has a rectangular shaped body, a pressure member for pressurizing a desired portion of human body, and a lamp located beneath the pressure member in the body for emitting far infrared light. A controller controls all functional components. Lifting means for raise and lower the thermal therapeutic devices to a predetermined height during a prescribed time period based upon an output signal of the controller. The lifting means have a lifting member, the upper portion of the lifting means passing through a hole of the upper housing.

16 Claims, 9 Drawing Sheets

AUTOMATIC THERMAL THERAPEUTIC APPARATUS

BACKGROUND OF THE INVENTION

1. Field of the Invention

The present invention relates to an automatic thermal therapeutic apparatus, more particularly to, an automatic thermal therapeutic apparatus, by which a user can treat desired portions of the user's body at any time without limit of the place and which can be collapsible to thereby be handy to carry.

2. Description of the Prior Art

In general, a thermal therapeutic apparatus for home use has a structure that a plurality of pressure members are mounted in a single device body for pressurizing certain spots of a human's body, and far infrared ray lamps are arranged in the pressure members and controlled by output signal from a control box. The far infrared ray lamp applies far infrared ray and heat lower than 60 degree to the spots on the human's body. The thermal therapeutic apparatus heats the human's body, facilitates the growth, strengthens the human's bone, keeps in an appropriate water, extracts waste matter from the human's body, resolves fat, protein and carbohydrate to maintain the nutritive balance condition, vibrates molecules and atoms of cells to keep the physical strength, and raises the temperature of hypodermic layers of the human's body to enlarge the capillary vessel and facilitate the circulation of the blood so that a metabolism is facilitated. By the above effects, the thermal therapeutic apparatus has been widely used in houses.

However, the conventional thermal therapeutic apparatus has several disadvantages as follows.

For using the thermal therapeutic apparatus for treating the desired portions of the human's body, the user must put one or more of the thermal therapeutic apparatuses on a bed or a chair and lie down or sit down on the bed or the chair in a state that the pressure members of the therapeutic apparatuses are located on the desired spot of the user's body to pressurize the desired spots.

Therefore, there is a restriction in the place because a wide place is required for the treatment, and the user cannot do any other works during the treatment.

Additionally, for treating all desired portions of the user's body, the user must move the thermal therapeutic apparatus from a portion to another portion on the user's body for allowing the pressure member to pressurize the desired portions. However, the user cannot find the desired portion exactly for himself and is in need of help from another person.

Recently, the thermal therapeutic apparatus which is applied to a bed or a chair has been widely used. However, the bed embedding the thermal therapeutic apparatus occupies a wide space and is very expensive.

Furthermore, the bed embedding the thermal therapeutic apparatus has a structure that a small-sized thermal therapeutic apparatus is embedded inside a large-sized elongated hole of the bed. Therefore, when the user or another person stands or lies on the bed, a portion of the user's body may fall into the hole of the bed, thereby injuring the user's body or damaging the thermal therapeutic apparatus.

In the meantime, the chair embedding the thermal therapeutic apparatus has been used for relaxation but cannot provide the function of the treatment.

SUMMARY OF THE INVENTION

Accordingly, it is an object of the present invention to provide a ground anchor overcoming the above enumerated difficulties.

It is another object of the present invention to provide a thermal therapeutic apparatus, which can automatically perform the treatment and the thermal treatment on all desired portions of a user's body when the user lies on a bed or a chair.

It is a further object of the present invention to provide a thermal therapeutic apparatus, which is collapsible for carrying.

It is still another object of the present invention to provide a thermal therapeutic apparatus, which is conveniently used at any place and any time without restriction of the place and the time.

It is yet another object of the present invention to provide a thermal therapeutic apparatus, which has an increased life and a reduced production cost.

To achieve the above objects, this invention provides an automatic thermal therapeutic apparatus comprising: an upper housing having a recess which has a predetermined width, length and depth on its center line in the longitudinal direction and a hole;

a lower housing positioned on the lower portion of the upper housing;

a plurality of thermal therapeutic devices positioned in the recess of the housing with the vertical movement, each thermal therapeutic device having a body made in about a rectangular shape by an injection molding of synthetic resin material, a pressure member for pressurizing a desired portion of human body and a lamp located beneath the pressure member in the body for generating far infrared ray;

fastening means situated between bottoms of the thermal therapeutic devices and the bottom surface of the recess, the fastening means having a pair of springs at opposite ends for fixing to opposite walls of the recess;

a controller for controlling all functional components; and lifting means for falling and rising the thermal therapeutic devices to a predetermined height during a prescribed period of time depending on output signal of the controller, the lifting means having a lifting member, the upper portion of the lifting means passing through the hole of the upper housing.

Other objects and benefits of the present invention will become apparent upon consideration of the following written description taken in conjunction with the accompanying figures.

BRIEF DESCRIPTION OF THE DRAWINGS

Understanding that these drawings depict only typical embodiments of the invention and are, therefore, not to be considered limiting of its scope, the invention will be described with additional specificity and detail through use of the accompanying drawings in which.

DETAILED DESCRIPTION OF THE INVENTION

Figure 1:
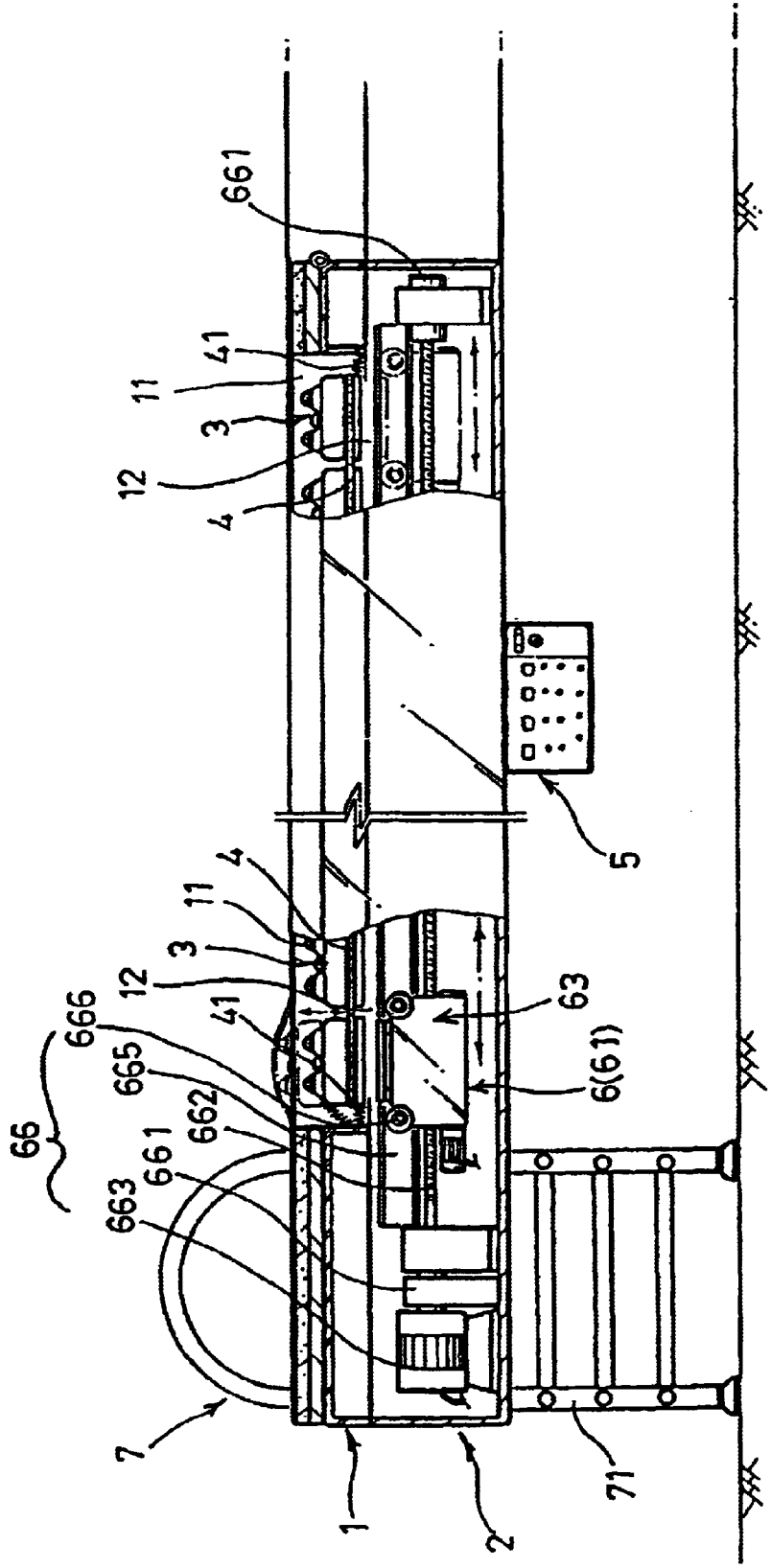
FIG. 1 is a front sectional view of a thermal therapeutic apparatus embedded inside a bed, according to a first preferred embodiment of the present invention.

The present invention will be described in detail hereinafter with reference to the accompanying drawings, wherein the same reference characters designate corresponding parts throughout several views. It is to be understood that these drawings depict only typical embodiments of the invention and are, therefore, not to be considered limiting of its scope.

Referring now to FIG. 1, an automatic thermal therapeutic apparatus includes: an upper housing 1 having a recess 11 which has a predetermined width, length and depth on its center line in the longitudinal direction and a hole 12; a lower housing 2 positioned on a lower portion of the upper housing 1; a plurality of thermal therapeutic devices 3 positioned in the recess 11 of the housing 1 with the vertical movement, each thermal therapeutic device 3 having a body 31 formed in a rectangular shape by an injection molding of synthetic resin material, a pressure member 32 for pressurizing a desired portion of a human's body and a lamp 33 located beneath the pressure member 32 in the body 31 for generating far infrared ray; fastening means 4 situated between bottoms of the thermal therapeutic devices 3 and the bottom surface of the recess 11, the fastening means 4 having a pair of springs 41 at opposite ends for fixing to opposite walls of the recess 11; a controller 5 for controlling all functional components; and lifting means 6 for falling and rising the thermal therapeutic devices up to a predetermined height in a settled period of time depending on output signal of the controller 5, the lifting means 6 having a lifting member 63.

The thermal therapeutic devices with the above structure can be applied to a bed 7 comprised of a frame 71 and a mat or applied to a chair which is comprised of a support member 81, a seat 82, a back of the chair 83 and a controller for adjusting an angle of the back of the chair 83.

The fastening means 4 is to maintain the thermal therapeutic devices 3 in the recess 11 at the regular intervals and the predetermined height and to lean the thermal therapeutic devices 3 positioned on both sides of the lifted thermal therapeutic device 3 at a prescribed angle during lifting the thermal therapeutic devices 3 in order. The fastening means 4 may adopt either a cord type belt or a timing belt, but the timing belt is better in consideration of an efficiency of installation and a fixing power on the thermal therapeutic device.

Because the ends of the fastening means 4 are fixed to both ends of the recess 11 through the springs 41, the thermal therapeutic devices 3 are in a certain interval from the bottom of the recess 11. When a user lies on the bed or the chair for treatment, the thermal therapeutic devices 3 which are arranged on the fastening means 4 at the regular intervals are kept the predetermined height from the bottom of the recess 11 by the elasticity of the springs 41.

Furthermore, when the user lies on the bed or the chair, the thermal therapeutic devices falls down somewhat, and at this time, one of the thermal therapeutic devices 3 rises upward to pressurize a portion of the user's body. Even though a portion of the fastening means 4 is bent upward with the thermal therapeutic device 3, since the springs 41 are expanded by the elasticity, the length of the fastening means 4 is not changed. After the treatment, when the user rises from the bed or the chair, the fastening means 4 is returned to its original condition.

There are two kinds of lifting means 6, i.e., movable type lifting means 61 and fixed type lifting means 62. The movable type lifting means 61 moves the lifting member 63 from one end to the other end of the lower housing 2 by transfer power generating means 66 driven in a predetermined time interval depending on the output signal of the controller 5. The movement of the lifting member 63 makes the thermal therapeutic devices 3 to rise and fall up to the settled height in order.

The fixed lifting means 62 has a plurality of lifting members 63 fixed to the bottom of the thermal therapeutic devices 3 respectively. The lifting members 63 of the fixed lifting means 62 are driven by the controller 5 in the predetermined interval of time in order.

The transfer power generating means 66 includes: a pair of idle bearings 661 mounted at opposite end portions on a longitudinal center line of the lower housing 2; a spiral rotary axle 662 located between the idle bearings 661; a DC motor 663 is connected to an end of the spiral rotary axle 662, the DC motor 663 having a decelerator therein; a power transmission means 664 screwed on the spiral rotary axle 662 for allowing the forward-backward movement of the lifting means 6 according to the driving direction of the DC motor 663; a pair of rails 665 arranged along the longitudinal direction of the lower housing 2; and wheels 666 arranged at front and rear portions of upper opposite sides of the lifting means 6 to roll along the rails 665 of the lower housing 2.

It will be appreciated that a gear in place of the bearing is directly located at one end portion of the lower housing 2, and a DC motor, in which has a reduction gear and which has a gear on its shaft, is located at the other end portion of the lower housing 2, and then a chain is arranged between the gears.

The lifting member 63 of the lifting means 6 may be comprised of an intake check valve 632, a discharge check valve 633, an operation lever 634, a support plate 65 place on the upper portion of the operation lever 634, and an air cylinder 631 operated by a compressor 10. Alternatively, the lifting member 63 of the lifting means 6 may be comprised of a rectangular body 635, a pair of X-shaped links 636, a power generating motor 638 arranged inside the rectangular body 635 and having a screw bar 637, a roller 640 mounted on the shaft 639 at the lower portion of a link of the X-shaped links 636, a lateral movement member 641 for allowing the support plate 65 to lift the thermal therapeutic devices 3 to the prescribed height by changing an angle of inclination of the links 636.

That is, the air cylinder 631 which changes the height of the operation lever 634 depending on an amount of air supplied from the compressor 10 and the power generating motor 638 which controls the angle of inclination of the X-shaped links 636 depending on the direction of the power supply are adopted as the lifting means 6. The operation lever 634 and the X-shaped links 636 are connected integrally with the support plate 65 for lifting the thermal therapeutic devices 3. In the latter case, because the components are so many and the rotation of the power generating motor 638 must be converted to the change of the inclination angle of the X-shaped links 636, the components are arranged inside the rectangular body 635 having a pair of rails 642.

Because the fixed type lifting means 62 has a structure that each lifting member 63 is placed at the lower portion of each thermal therapeutic device 3, it is operated exactly and has a reduced noise, while the production cost is increased. Because the movable type lifting means 61 uses the single lifting member 63 with the transfer power generating means 66, the production cost is reduced, while the mechanical structure is complicate and noise is occurred. Therefore, the user may select one of two embodiments in consideration of the place for use and characteristics of the product.

Meanwhile, the transfer power generating means 66 of the movable lifting means 61 includes: the pair of idle bearings 661 mounted at opposite end portions on the longitudinal center line of the lower housing 2; the spiral rotary axle 662 located between the idle bearings 661; the DC motor 663 is connected to an end of the spiral rotary axle 662, the DC motor 663 having a decelerator therein; the power transmission means 664 screwed on the spiral rotary axle 662 for allowing the forward-backward movement of the lifting means 6 according to the driving direction of the DC motor 663; the pair of rails 665 arranged along the longitudinal direction of the lower housing 2; and the wheels 666 arranged at front and rear portions of upper opposite sides of the lifting means 6 to roll along the rails 665 of the lower housing 2. When the movable lifting means 61 is moved laterally by the DC motor 663 and the thermal therapeutic devices 3 are raised in state that the weight of the human's body is applied, most of the weight is applied to the rails 665, thereby preventing the spiral rotary axle 662 from being bent.

It will be appreciated that the transfer power generating means 66 is not limited by the above structure, and that another methods such as a chain form or a link form can be adopted.

In case that the air cylinder 631 is adopted as the lifting member 63 of the lifting means 6, when the thermal therapeutic devices 3 are fixed at a certain location by the output signal of the controller 5 or by the transfer power generating means 66, the discharge check valve 633 of the air cylinder 631 is shut and the intake check valve 632 is opened to allow the air to flow into the cylinder from the outside. The operation lever 634 of the air cylinder 631 is moved outward depending on an amount of air flown into the air cylinder 631, so that the support plate 65 mounted at the lower portion of the operation lever 634 is raised and the thermal therapeutic devices 3 are risen to the prescribed height.

At this time, for differentiating the pressure against each portion of the user's body, the height of each thermal therapeutic device can be set at the user's disposal by using a volume allowing the user to change the program within the controller 5. If the user regulates the volume properly, the open and close time of the intake check valve 632 is changed.

When the thermal therapeutic device 3 is risen to the desired height by the air cylinder 631, the intake check valve 632 of the air cylinder is closed by the controller 5. The height of the thermal therapeutic device is maintained until the discharge check valve 633 is opened. As the prescribed period of time passes, when the discharge check valve 633 of the air cylinder 631 is opened by the controller 5 and the air filling the cylinder is discharged, the thermal therapeutic device falls down with the operation lever 634 of the air cylinder 631.

Figure 2:
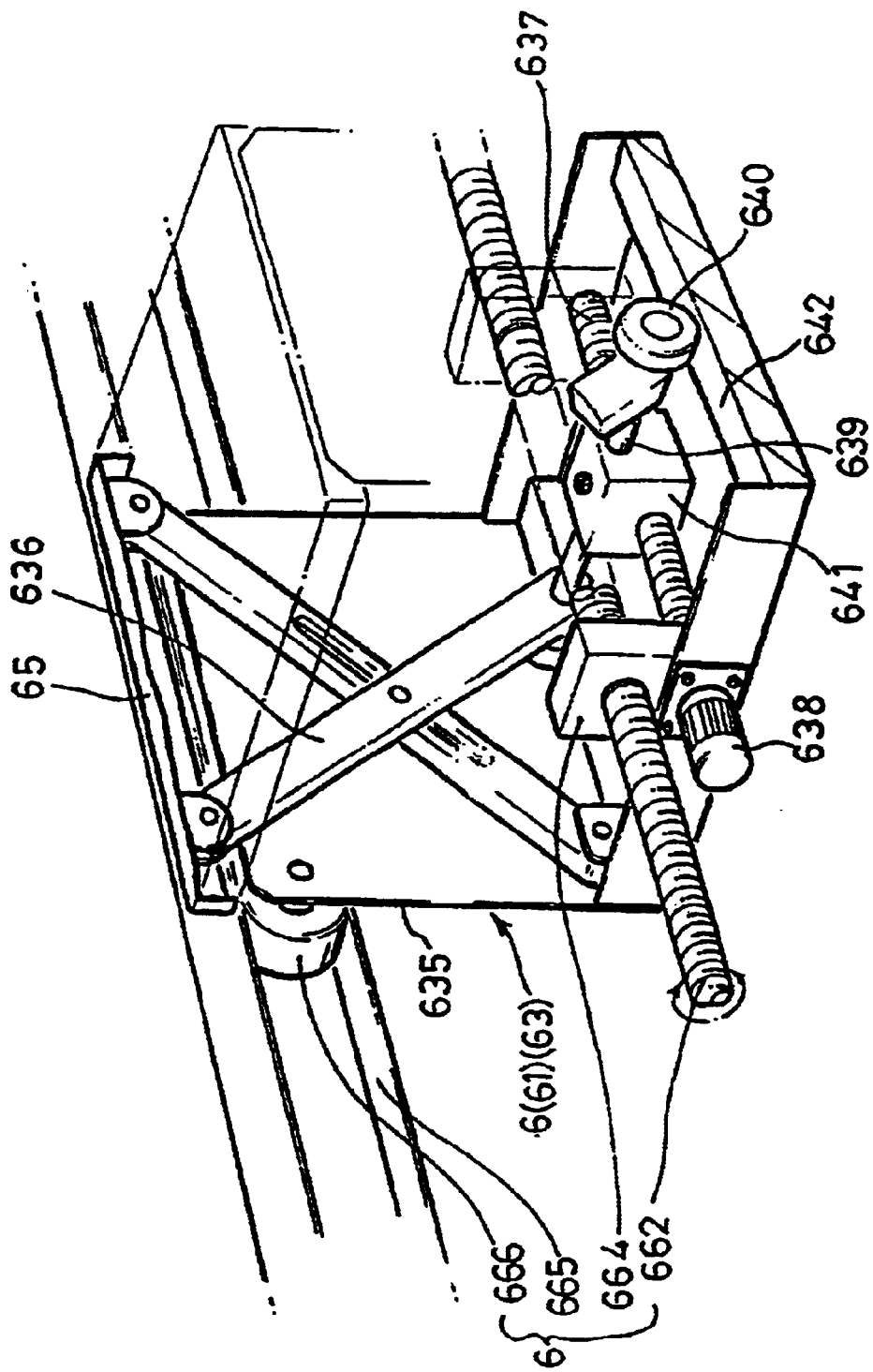
FIG. 2 is an enlarged perspective view of the first embodiment of the present invention.
Figure 3:
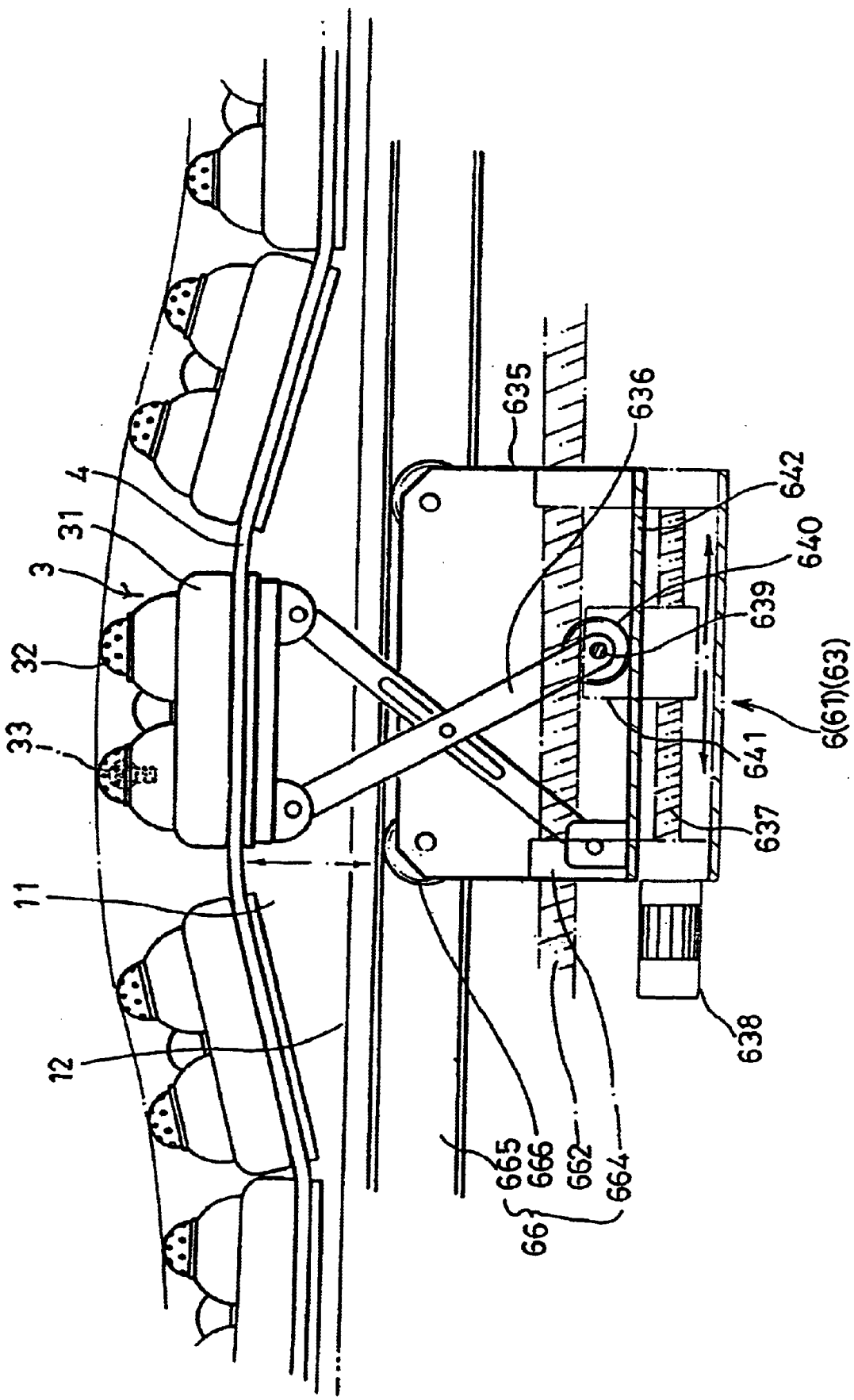
FIG. 3 is an enlarged front sectional view of an operation state of the first embodiment of the present invention.
Figure 4:
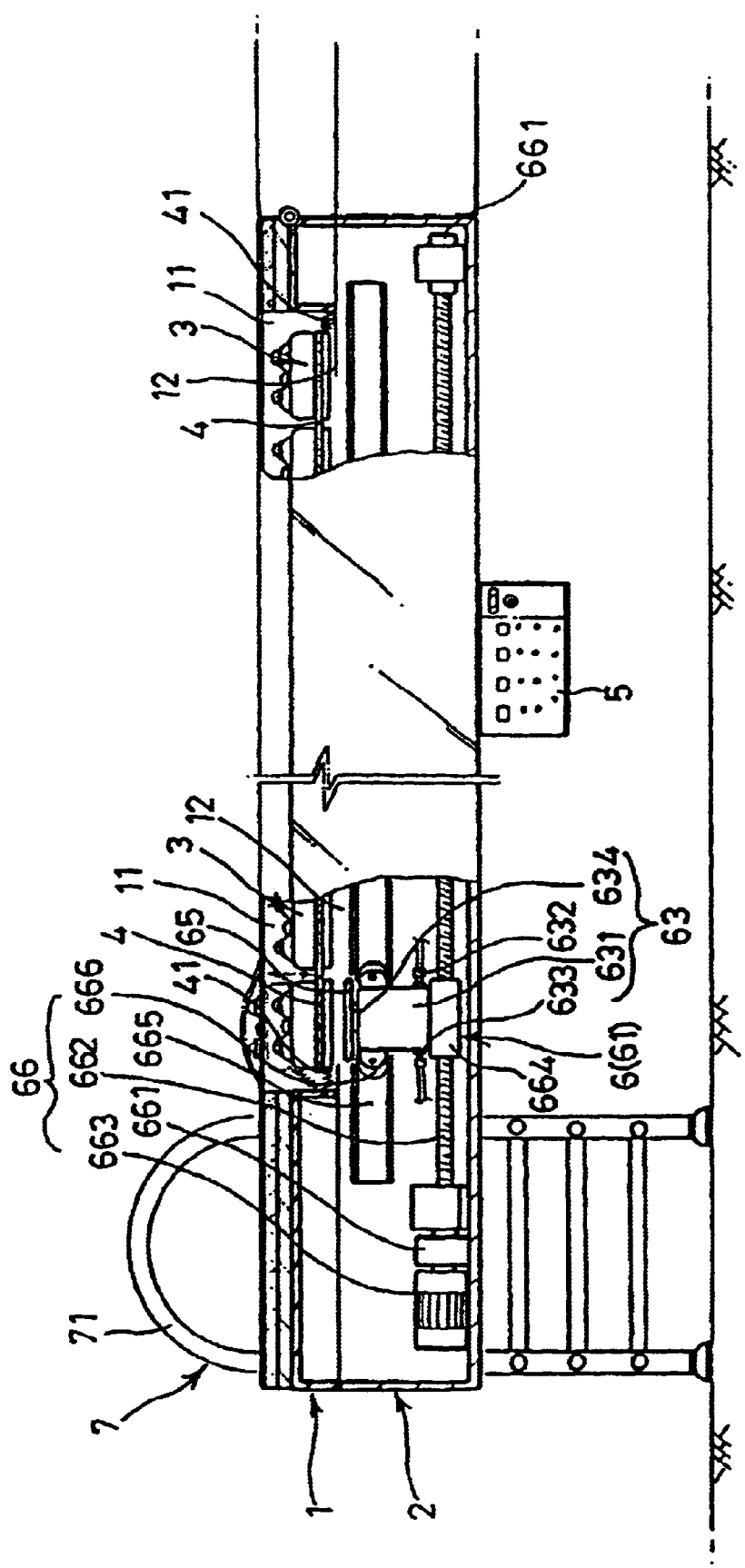
FIG. 4 is a front sectional view a thermal therapeutic apparatus embedded in the bed, according to a second preferred embodiment of the present invention.
Figure 5:
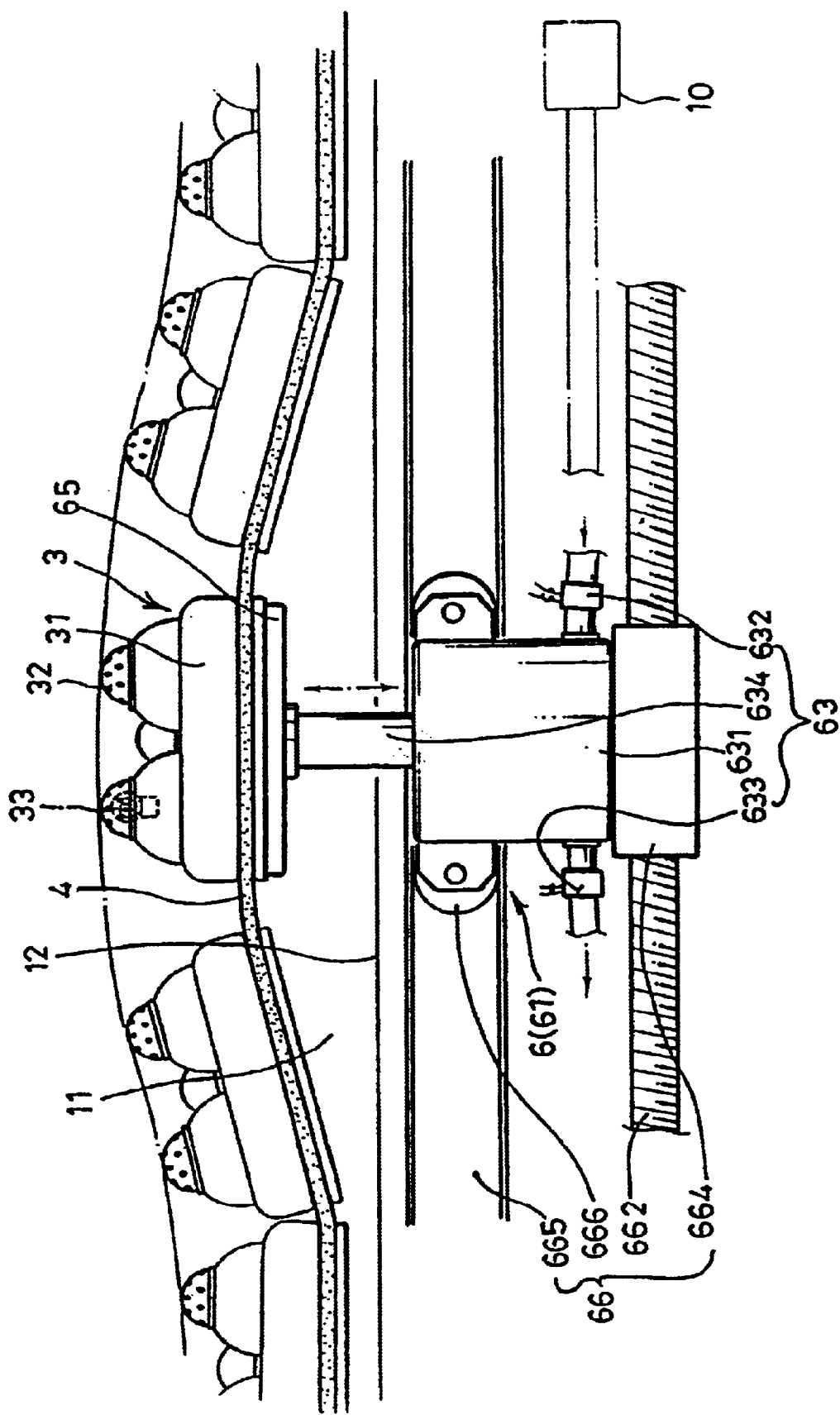
FIG. 5 is an enlarged front sectional view of an operation state of the second embodiment of the present invention.
Figure 6:
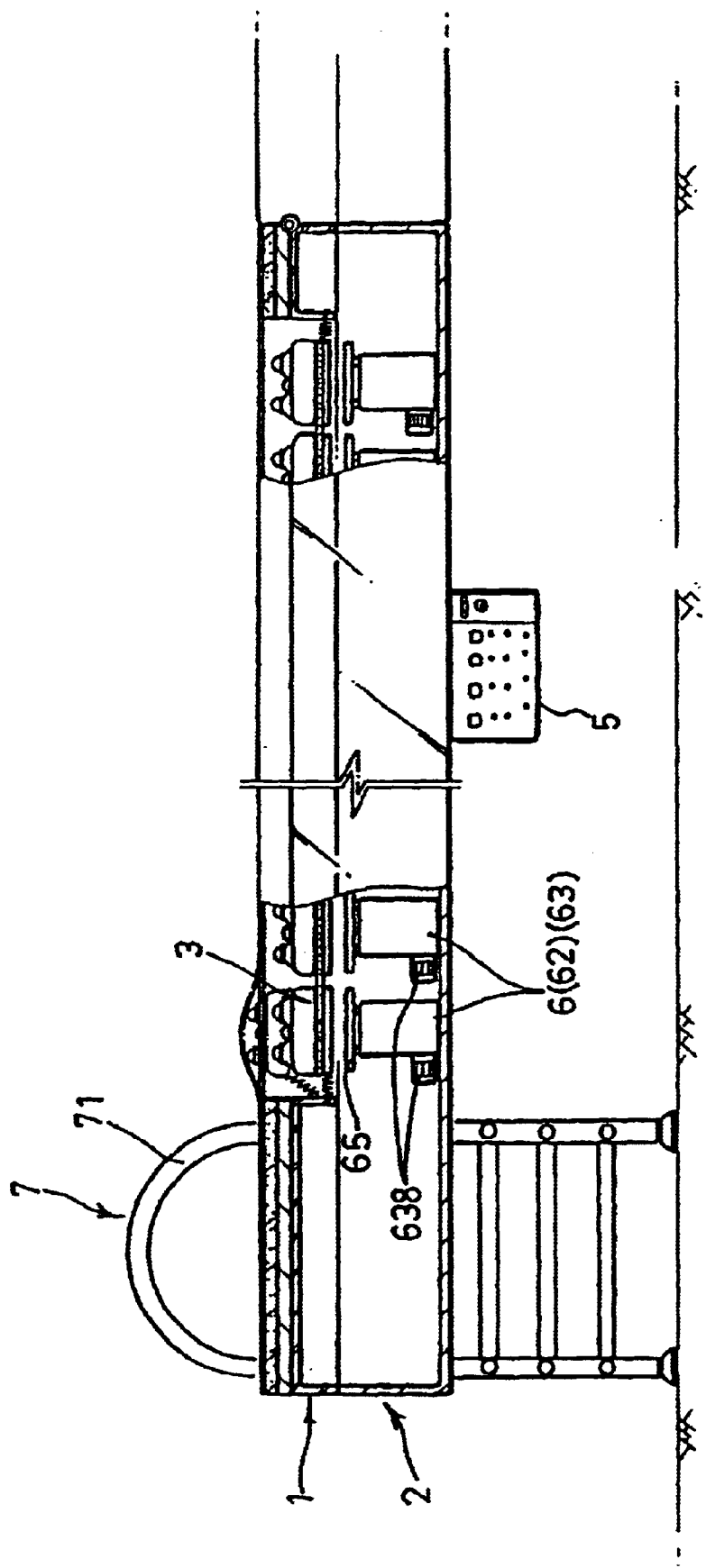
FIG. 6 is a front sectional view a thermal therapeutic apparatus embedded in the bed, according to a third preferred embodiment of the present invention.
Figure 7:
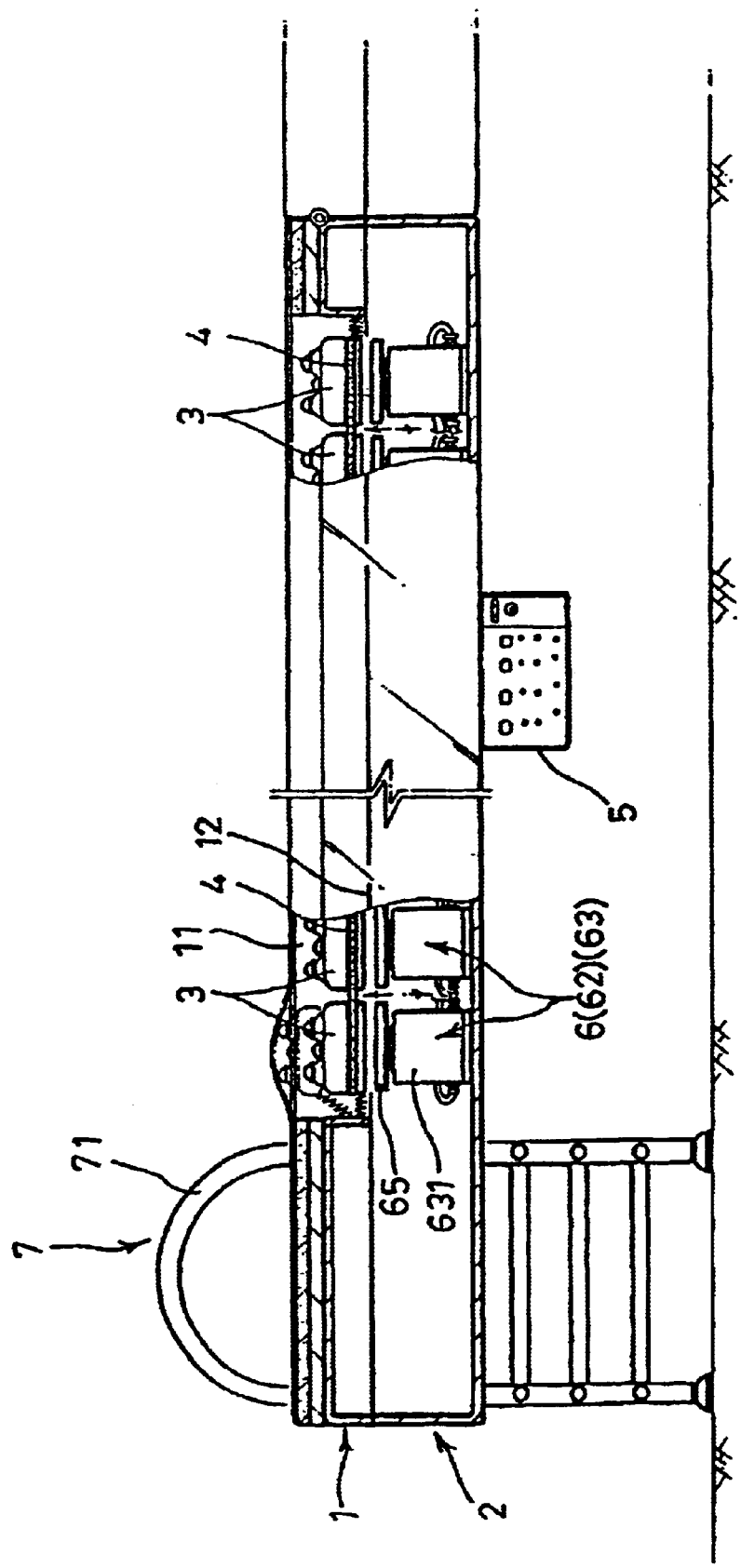
FIG. 7 is a front sectional view a thermal therapeutic apparatus embedded in the bed, according to a fourth preferred embodiment of the present invention.
Figure 8:
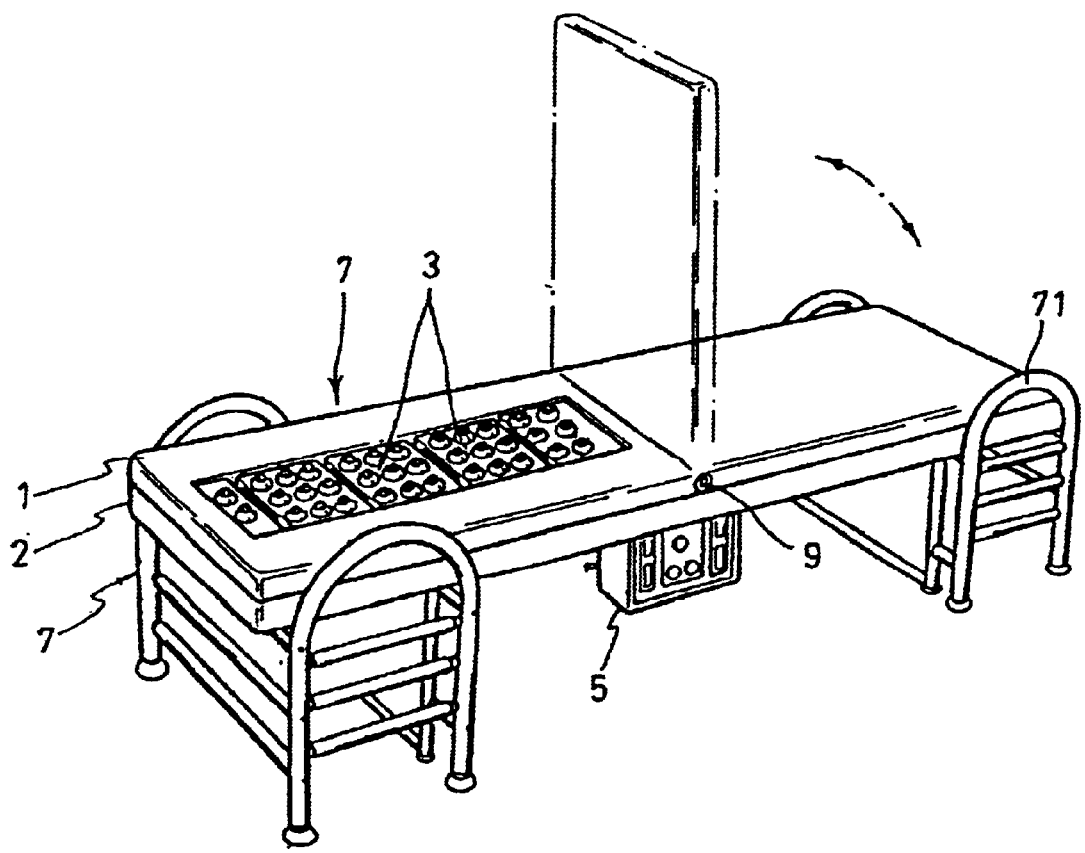
FIG. 8 is a perspective view of the thermal therapeutic apparatus applied to the bed.
Figure 9:
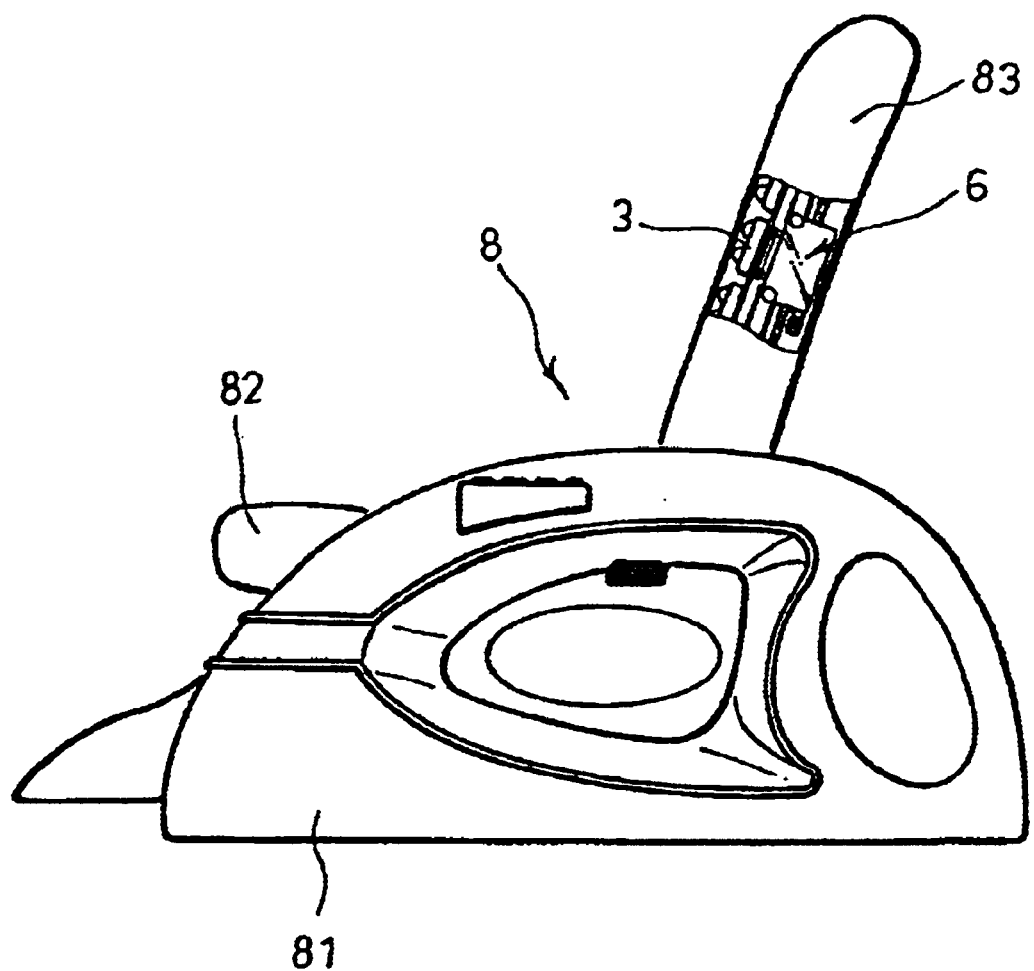
FIG. 9 is a perspective view of the thermal therapeutic apparatus applied to a chair.

In case that the power generating motor 638 is adopted as the lifting member 63 of the lifting means 6, when the power generating motor 638 is rotated in the counterclockwise direction depending on the output signal of the controller 5, the screw bar 637 connected to the axle thereof is also rotated in the counterclockwise direction to thereby move a movable member 641 screwed with the screw bar 637 to the left direction of FIG. 2. At this time, a shaft 639 connected to the movable member 641 pulling the lower portion of the link 636 to the left direction by the rolling movement of the wheel 666 so that the X-shaped links 636 has a reduced angle of inclination. The support plate 65 connected on the upper portion of the links 636 is risen and the thermal therapeutic device 3 arranged on the support plate 65 is also risen to the prescribed height. The height of the thermal therapeutic device is determined by a rotary amount of the power generating motor 638 which is controlled by the controller 5.

When the thermal therapeutic device 3 is risen to the desired height by the movement of the power generating motor 638, the screw bar 637, the movable member 641, the X-shaped links 636 and the support plate 65, the power generating motor 638 is stopped by the controller 5. The thermal therapeutic device 3 is kept in the desired height until the set time passes. When the power generating motor 638 of the lifting means 6 is rotated in the clockwise direction by the controller 5, the screw bar is also rotated in the clockwise direction and the movable member 641 screwed with the screw bar 637 moves the shaft of the link 636 to the right direction. The angle of inclination of the X-shaped links 636 is enlarged and the support plate 65 falls down with the thermal therapeutic device 3. At this time, the X-shaped links 636 are returned to their original condition by the rotary amount of the power generating motor 638 controlled by the controller 5.

In the meantime, the lifting means 6, which moves along the longitudinal direction of the lower housing 2 by the transfer power generating means 66, is moved during a prescribed period of time depending on the interval of the thermal therapeutic devices. The distance of movement is also determined by the rotary amount of the DC motor 663 controlled by the controller 5. Generally, the controller 5 rotates the DC motor 663 on the spiral rotary axle 662 by a previously set data.

That is, when the controller 5 outputs the operation signal of the clockwise direction or the counterclockwise direction at the prescribed period of time, the DC motor 663 rotates the prescribed number of rotation in the clockwise direction or the counterclockwise direction and the spiral rotary axle 662 arranged between the idle bearings 661. The power transmission means 664 screwed on the spiral rotary axle 662 is moved forward or backward along the spiral rotary axle 662 and the movable type lifting means 61 is moved forward or backward to the prescribed distance (namely, the set interval of the thermal therapeutic devices) along the rails 665.

The controller 5 stores all control program such as a lighting of the thermal therapeutic devices, a heat temperature, the operation timing of the lifting means 6 and transfer power generating means 66, the height of the thermal therapeutic device or the likes to control all operation process.

If necessary, the user can lift only the desired thermal therapeutic device during a desired period of time using a manipulation button of the controller 5. The control method is obtained by changing the control program.

The automatic thermal therapeutic devices according to the present invention can be applied to a bed 7 which is comprised of a frame 71 and a mat or applied to a chair 8 which is comprised of a support member 81, a seat 82, a back of the chair 83 and means for regulating an angle of the back of the chair 83.

When the user lies on the bed 7 or the chair 8 embedding the thermal therapeutic devices 3, the thermal therapeutic devices 3 are operated and perform the automatic physical treatment on all desired portion of the user's body, thereby improving the treatment effects.

In case of the bed 7 embedding the thermal therapeutic devices 3, the upper and lower housings 2 are divided into two parts, one has the thermal therapeutic devices 3 and the other does not have the thermal therapeutic devices 3. A hinge 9 is placed on a contact portion thereof. When carrying, the bed 7 is folded in the center of the hinge 9, thereby preventing the damage of the thermal therapeutic devices 3.

Those skilled in the art will readily recognize that these and various other modifications and changes may be made to the present invention without strictly following the exemplary application illustrated and described herein, and without departing from the true spirit and scope of the present invention, which is set forth in the following claims.

What is claimed is:

1. An automatic thermal therapeutic apparatus, comprising:
    an upper housing having a recess defined by a predetermined width, length and depth, relative to a center line in a longitudinal direction, and a hole;
    a lower housing positioned on a lower portion of the upper housing;
    a plurality of thermal therapeutic devices positioned in the recess of the upper housing, each thermal therapeutic device having a rectangular body, a pressure member for applying pressure to a desired portion of human body and a lamp located beneath the pressure member in the body for generating far infrared radiation;
    fastening means situated between bottoms of the thermal therapeutic devices and the bottom surface of the recess, the fastening means having a pair of springs at opposite ends for fixing to opposite walls of the recess;
    a controller for controlling all functional components; and
    lifting means for lowering and raising the thermal therapeutic devices to a predetermined height during a prescribed period of time depending on output signal of the controller, the lifting means having a lifting member, the upper portion of the lifting means passing through the hole of the upper housing.

2. An automatic thermal therapeutic apparatus as claimed in claim 1, wherein the lifting member of the lifting means includes an intake check valve and a discharge check valve that are opened and shut by the controller, an operation lever, a support plate located on an upper portion of the operation lever, and an air cylinder allowing the support plate and the thermal therapeutic device to rise and fall using air supplied from a compressor.

3. An automatic thermal therapeutic apparatus as claimed in claim 1, wherein the lifting member of the lifting means includes a rectangular body, a pair of X-shaped links, a power generating motor arranged inside the rectangular body and having a screw bar, a roller mounted on the shaft at the lower portion of a link of the X-shaped links the roller performing a rolling movement along rails arranged on the bottom of the rectangular body, a lateral movement member for lifting the support plate to lift the thermal therapeutic device to a prescribed height by changing an angle of inclination of the links.

4. An automatic thermal therapeutic apparatus as claimed in claim 3, wherein the upper and the lower housings containing the thermal therapeutic devices are disposed in a bed.

5. An automatic thermal therapeutic apparatus as claimed in claim 3, wherein the upper and the lower housings containing the thermal therapeutic devices are disposed in a collapsible chair which includes a support member, a seat, a back of the chair and means for regulating the back the chair.

6. An automatic thermal therapeutic apparatus as claimed in claim 1, wherein the lifting means includes a movable type lifting means which moves the lifting member within the lower housing by the operation of a transfer power generating means driven during a predetermined interval of time depending on an output signal of the controller, thereby raising and lowering the thermal therapeutic devices to the predetermined height.

7. An automatic thermal therapeutic apparatus as claimed in claim 6, wherein the transfer power generating means of the movable type lifting means includes:
    a pair of idle bearings mounted at opposite end portions of the lower housing;
    a spiral rotary axle located between the idle bearings;
    a DC motor connected to an end of the spiral rotary axle, the DC motor having a decelerator therein;
    a power transmission means screwed on the spiral rotary axle for producing forward and backward movement of the lifting means according to the driving direction of the DC motor;
    a pair of rails arranged along the longitudinal direction and disposed in the lower housing; and
    wheels located at front and rear portions of upper opposite sides of the lifting means which roll along the pair of rails.

8. An automatic thermal therapeutic apparatus as claimed in claim 7, wherein the upper and the lower housings containing the thermal therapeutic devices are disposed in a bed.

9. An automatic thermal therapeutic apparatus as claimed in claim 7, wherein the upper and the lower housings containing the thermal therapeutic devices are disposed in a collapsible chair which includes a support member, a seat, a back of the chair and means for regulating the back the chair.

10. An automatic thermal therapeutic apparatus as claimed in claim 6, wherein the upper and the lower housings containing the thermal therapeutic devices are disposed in a bed.

11. An automatic thermal therapeutic apparatus as claimed in claim 6, wherein the upper and the lower housings containing the thermal therapeutic devices are disposed in a collapsible chair which includes a support member, a seat, a back of the chair and means for regulating the back the chair.

12. An automatic thermal therapeutic apparatus as claimed in claim 1, wherein the lifting means includes a fixed type lifting means which lifting member is fixed to the bottom of each thermal therapeutic device, and each lifting means fixed to each thermal therapeutic device is driven by the controller during a predetermined interval of time.

13. An automatic thermal therapeutic apparatus as claimed in claim 12, wherein the upper and the lower housings containing the thermal therapeutic devices are disposed in a bed.

14. An automatic thermal therapeutic apparatus as claimed in claim 12, wherein the upper and the lower housings containing the thermal therapeutic devices are disposed in a collapsible chair which includes a support member, a seat, a back of the chair and means for regulating the back the chair.

15. An automatic thermal therapeutic apparatus as claimed in claim 1, wherein the upper and the lower housings containing the thermal therapeutic devices are disposed in a bed.

16. An automatic thermal therapeutic apparatus as claimed in claim 1, wherein the upper and the lower housings containing the thermal therapeutic devices are disposed in a collapsible chair which includes a support member, a seat, a back of the chair and means for regulating the back the chair.

* * * * *